United States Patent
Haisch et al.

(10) Patent No.: US 12,137,957 B2
(45) Date of Patent: Nov. 12, 2024

(54) FLUID CONTROL ARRANGEMENT FOR A MEDICAL DEVICE

(71) Applicant: Erbe Elektromedizin GmbH, Tuebingen (DE)

(72) Inventors: Philipp Haisch, Tuebingen (DE); Uwe Dawidowsky, Rottenburg (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 595 days.

(21) Appl. No.: 16/828,020

(22) Filed: Mar. 24, 2020

(65) Prior Publication Data

US 2020/0309576 A1 Oct. 1, 2020

(30) Foreign Application Priority Data

Mar. 25, 2019 (EP) .................................... 19164955

(51) Int. Cl.
*A61B 18/04* (2006.01)
*A61B 18/00* (2006.01)

(52) U.S. Cl.
CPC ............ *A61B 18/042* (2013.01); *A61B 18/00* (2013.01); *A61B 2018/00589* (2013.01); *A61B 2018/00636* (2013.01); *A61B 2018/044* (2013.01); *A61M 2205/3334* (2013.01)

(58) Field of Classification Search
CPC . A61B 18/00; A61B 18/1402; A61B 18/1445; A61B 17/295; A61B 2018/042; A61B 2018/0044; A61B 2018/00589; A61B 2018/00636; A61M 2205/3334
See application file for complete search history.

(56) References Cited

U.S. PATENT DOCUMENTS

| | | |
|---|---|---|
| 3,490,337 A | 1/1970 | Klein |
| 5,020,373 A | 6/1991 | Kamiunten et al. |
| 5,888,390 A | 3/1999 | Craig |
| 8,414,570 B2 | 4/2013 | Turner et al. |
| 9,371,933 B2 | 6/2016 | Nitta |
| 9,374,891 B2 | 6/2016 | Bartulec et al. |

(Continued)

FOREIGN PATENT DOCUMENTS

| | | |
|---|---|---|
| CN | 102711643 A | 10/2012 |
| DE | 195 46 535 A1 | 6/1997 |

(Continued)

*Primary Examiner* — Michael F Peffley
*Assistant Examiner* — Samantha M Good
(74) *Attorney, Agent, or Firm* — Blank Rome LLP

(57) ABSTRACT

A fluid control arrangement for a medical device. The fluid control arrangement has a fluid control circuit with at least one fluid control component, through which a fluid flows. For controlling the at least one fluid control component, a control circuitry with at least one electric and/or electronic component is provided. A first carrier part has a first coupling surface and a second carrier part has a second coupling surface. In the first coupling surface at least one first fluid channel cavity and/or in the second coupling surface at least one second fluid channel cavity is provided. By connecting the carrier parts with each other with facing coupling surfaces, at least one main fluid channel is formed in the area of the separating location. At the first carrier part a first mounting surface for the at least one fluid control component can be provided.

14 Claims, 6 Drawing Sheets

(56) References Cited

U.S. PATENT DOCUMENTS

| | | | |
|---|---|---|---|
| 9,579,654 B2 | 2/2017 | Schultz | |
| 9,867,935 B2 | 1/2018 | Chappel | |
| 2003/0069576 A1* | 4/2003 | Tanrisever | H05H 1/48 606/41 |
| 2005/0011282 A1* | 1/2005 | Voege | A61M 16/0841 73/861.44 |
| 2015/0208497 A1 | 7/2015 | Bartulec et al. | |
| 2017/0059376 A1 | 3/2017 | Bochenko | |
| 2018/0335331 A1 | 11/2018 | Clinger | |
| 2019/0083161 A1* | 3/2019 | Harle | H05H 1/2406 |

FOREIGN PATENT DOCUMENTS

| | | |
|---|---|---|
| DE | 101 27 261 A1 | 12/2002 |
| JP | H10267199 A | 10/1998 |
| JP | H11125378 A | 5/1999 |
| JP | 2002016340 A | 1/2002 |
| RU | 2479863 C2 | 4/2013 |
| RU | 2526261 C2 | 8/2014 |
| RU | 2628984 C1 | 8/2017 |
| RU | 2667045 C2 | 9/2018 |
| SU | 1435945 A1 | 11/1988 |
| WO | WO-99/36747 A1 | 7/1999 |

\* cited by examiner

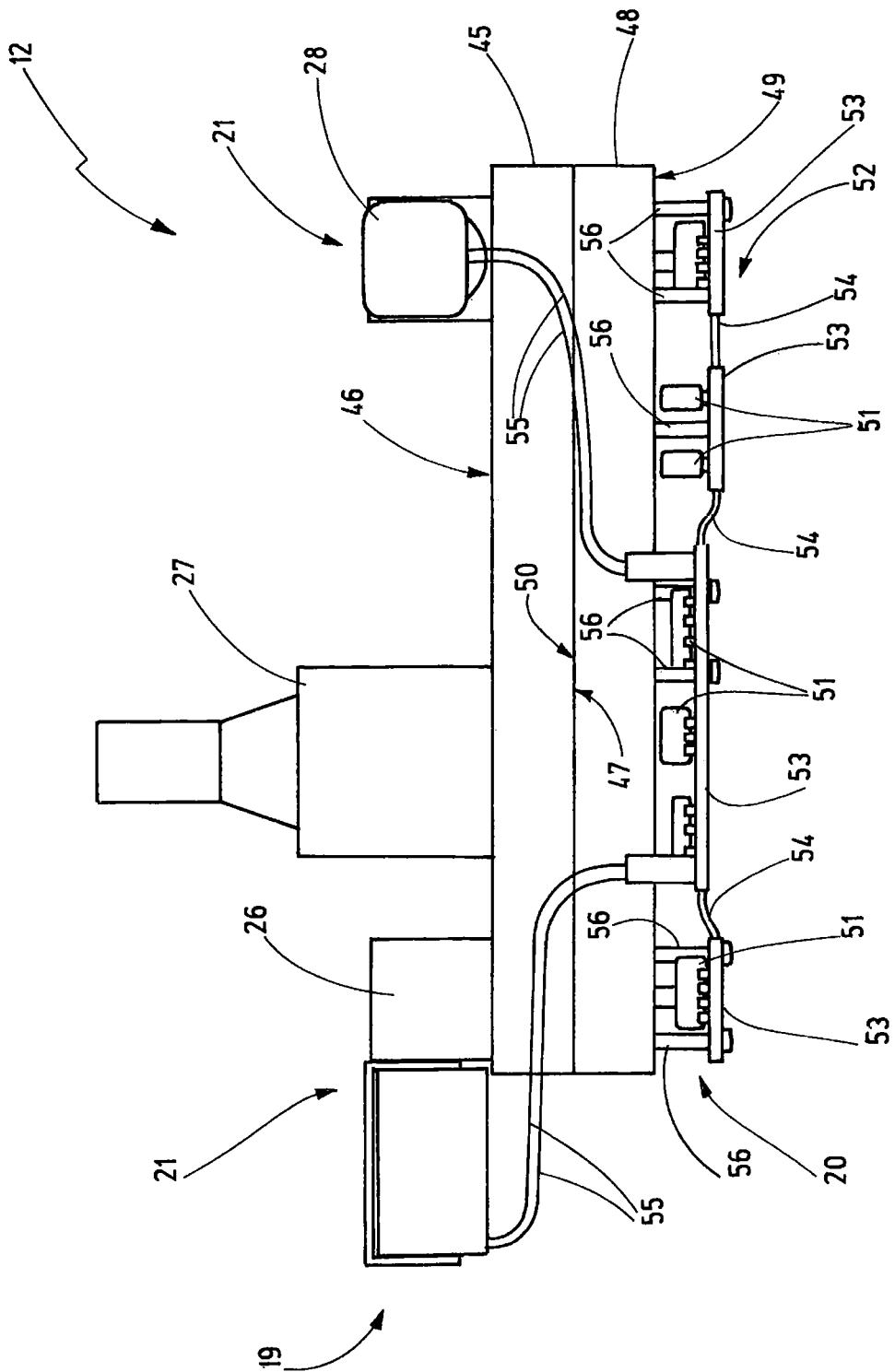

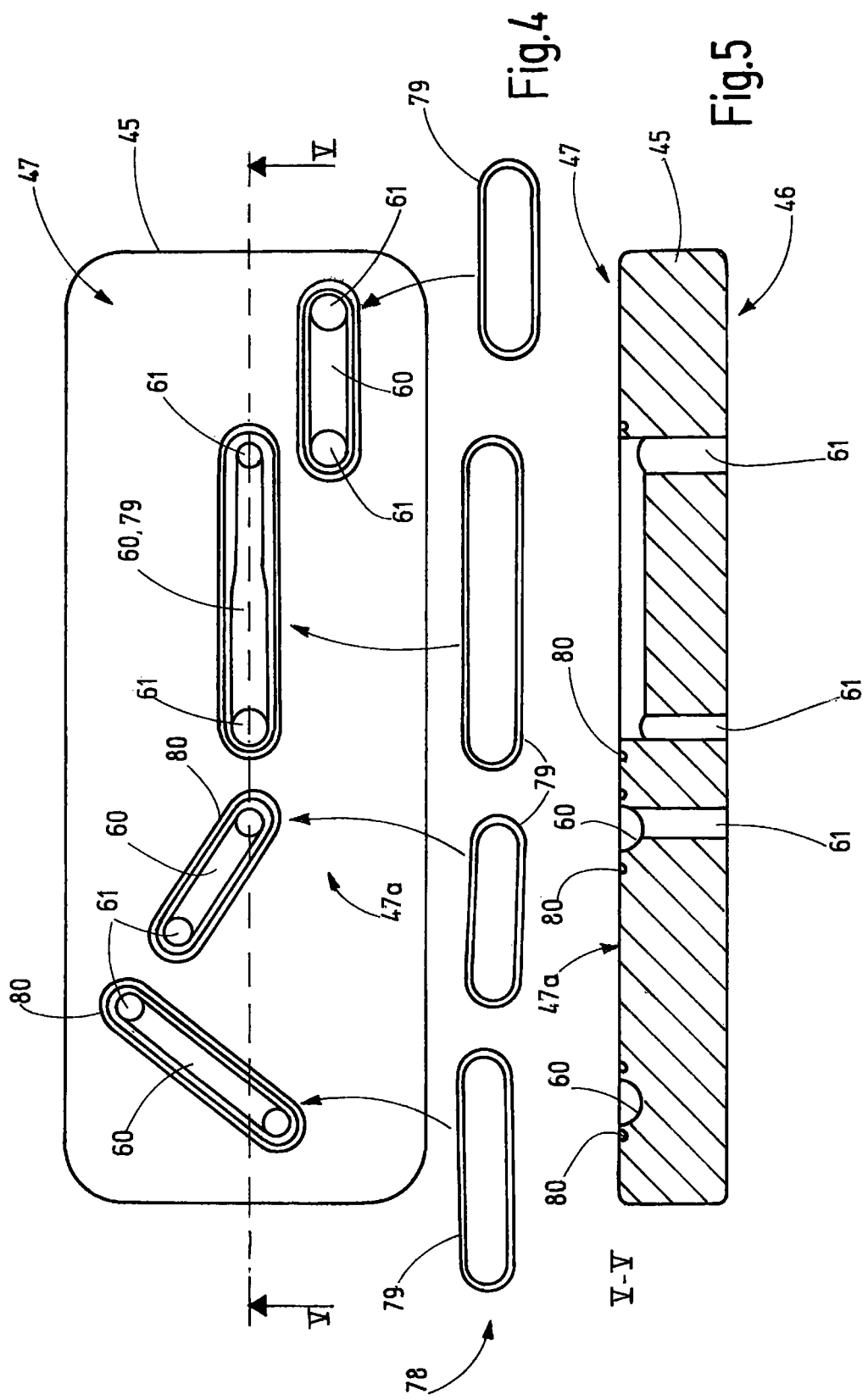

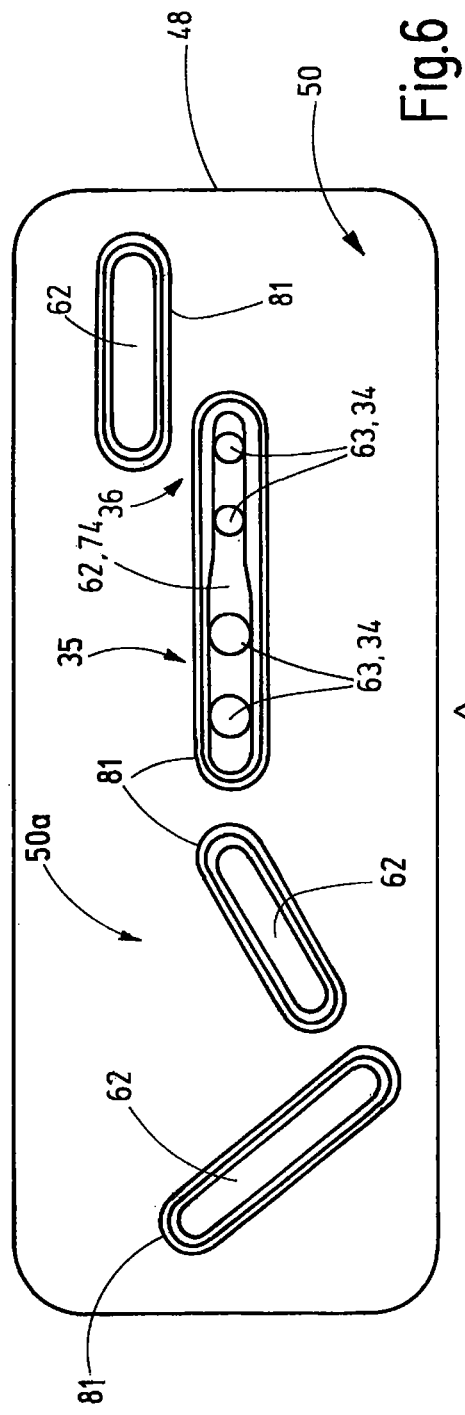
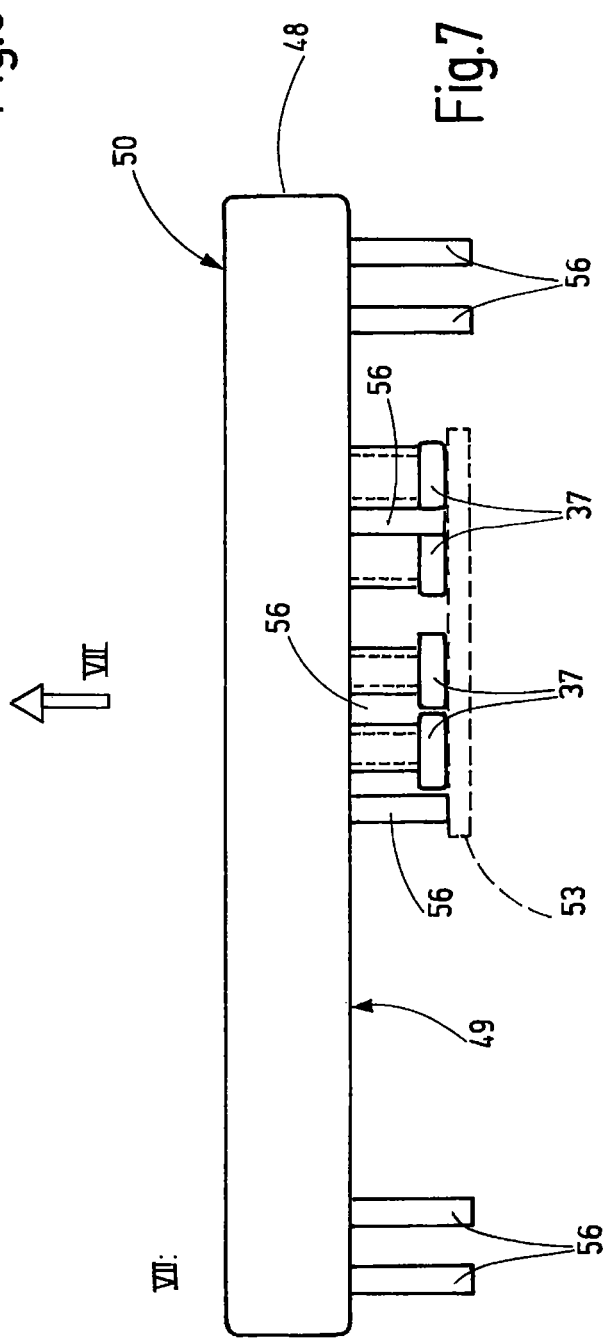

FLUID CONTROL ARRANGEMENT FOR A MEDICAL DEVICE

CROSS-REFERENCE TO RELATED APPLICATION

This application claims the benefit of European Patent Application No. 19164955.7 filed on Mar. 25, 2019, the contents of which is incorporated by reference herein.

TECHNICAL FIELD

The invention refers to a fluid control arrangement for a medical device. By means of the fluid control arrangement, the volume flow or mass flow of a fluid, particularly a gas for medical applications, can be controlled or feedback controlled.

BACKGROUND

Devices for fluid control are known from different technical fields. U.S. Pat. No. 5,888,390 A describes a miniature arrangement of foldable connected metallic plates in the respective inner sides thereof fluid channel cavities are etched. By folding, a multiple layer body is created in order to conduct fluids. This arrangement is suitable for analytic devices due to the miniaturization, e.g. for chromatographs.

DE 195 46 535 A1 discloses a method and a device for sample extraction with integrated analytic chemical sensor measurement and a method for manufacturing the device. A measurement cartridge is equipped with chemo- or biosensors and can be arranged between needle and syringe by Luer connections. After the sample extraction by means of the syringe the measurement cartridge can be inserted into a hand measuring device.

A flow measurement device is known from U.S. Pat. No. 5,020,373 A that comprises a flow sensor that is arranged in a channel section of a flow channel with reduced diameter. In flow direction downstream a swirl creator, as well as a pressure measurement channel are arranged. The created swirl frequencies are a function of the flow rate that can be detected via the pressure measurement channel.

WO 99/36747 A1 discloses a device and a method for detection of a fluid flow as a function of a pressure difference between two connections in a flow channel.

Starting from the prior art it can be considered as object of the present invention to provide an improved fluid control arrangement for a medical device. Particularly, the fluid control arrangement shall be configured to control a gas flow of a medical gas and in doing so, to allow a compact and cheap configuration.

SUMMARY

This object is solved with a fluid control arrangement, for example, according to the features of claim 1.

The fluid control arrangement is particularly configured to control or feedback control a gas flow of a gas such as argon, oxygen, carbon dioxide or another gas used in a medical device. Instead of a gas flow also a liquid flow can be controlled or feedback controlled in other medical applications. The medical device can be particularly a device for argon plasma coagulation.

The fluid control arrangement has a fluid control circuit comprising a fluid channel arrangement and at least one fluid control component. The fluid channel arrangement and the fluid control component are arranged between an inlet connection and an outlet connection and form together a fluidic connection between the inlet connection and the outlet connection. Preferably, during operation of the fluid control arrangement, a fluid flows through the at least one fluid control component or through all of the provided fluid control components. A fluid control component can be, e.g. a way valve, a proportional valve, a pressure control valve or a pressure regulation valve, a filter or another component, through which a fluid can flow that does not only channel the fluid, but modifies additionally a fluid characteristic (e.g. pressure, volume flow, mass flow, purity) of the fluid channeled therethrough.

A control circuitry is configured to control the at least one fluid control component of the fluid control circuit. For this the control circuitry comprises at least one electric and/or electronic component comprising, e.g. a control unit that provides control signals for the at least one fluid control component. Preferably the control circuitry does not contain any component through which a fluid flows. One or more components of the control circuitry, e.g. pressure sensors, can be in contact with the fluid, but preferably no fluid flows therethrough.

The fluid control arrangement comprises a first carrier part with a first mounting surface at a first coupling surface, as well as a second carrier part with a second mounting surface and a second coupling surface. The mounting surface and the coupling surface of a respective carrier part are preferably arranged on opposite sides of the respective carrier part. In an embodiment the first mounting surface and/or the second mounting surface extend in a respective plane. The first mounting surface is configured for mounting of the at least one fluid control component. The second mounting surface is configured for mounting the at least one electric and/or electronic component of the control circuitry. A fluid control component or multiple fluid control components of the fluid control circuit are arranged at the first mounting surface of the first carrier part and/or a component or multiple components of the control circuitry are arranged at the second mounting surface of the second carrier part. It is preferred that all of the fluid control components of the fluid control circuit and/or all of the components of the control circuitry are directly or indirectly arranged at the respective mounting surface.

In an embodiment some or multiple of the provided fluid control components are directly arranged at the first mounting surface and are fluidically connected with the fluid channel arrangement. At the second mounting surface a circuit board arrangement can be attached that supports the at least one electric and/or electronic component of the control circuitry. Preferably all of the electric and/or electronic components of the control circuitry are arranged at the circuit board arrangement.

It is also advantageous, if no components are attached to the first carrier part and/or the second carrier part outside of the respective mounting surface.

For creating the at least one main fluid channel of the fluid channel arrangement at least one first fluid channel cavity is provided in the first coupling surface and/or at least one second fluid channel cavity is provided in the second coupling surface. The at least one main fluid channel thus extends along the separation plane between the first coupling surface and the second coupling surface. In circumferential direction the at least one main fluid channel is limited partly by the first coupling surface and partly by the second coupling surface. In the area of the first coupling surface and the second coupling surface, the first carrier part and the second carrier part are connected with each other. The coupling surfaces can have a preferably planar surface section respectively that can be in direct two-dimensional contact or that are facing each other under creation of a gap. These surface sections surround the fluid channel cavities of the carrier parts. The at least one first and second fluid channel cavity is deepened in relation to the surrounding surface section of the first and second coupling surface. If the two carrier parts are connected with each other in the area of their coupling surfaces, the first fluid channel cavity limits together with the second carrier part and/or the second fluid channel cavity limits together with the first carrier part a main fluid channel in the area of the separating location between the two carrier parts. The carrier parts are connected in the area of the coupling surfaces with each other such that the at least one main fluid channel is fluidically sealed in the area of the separation location between the two carrier parts, under use of a seal arrangement as an option.

The at least one main fluid channel is exclusively present in the area of the separating location or the separating plane between the carrier parts and limited by both carrier parts, particularly along its total extension. Particularly the at least one main fluid channel is limited along its complete extension by a channel wall of the first carrier part and by a channel wall of the second carrier part concurrently. Additional fluid channels of the fluid channel arrangement can extend within the first carrier part and/or the second carrier part and can particularly form branch channels from or to a fluid channel cavity. Preferably all of the fluid channels of the fluid channel arrangement are limited by channel walls that are either integral part of the first carrier part or integral part of the second carrier part. Within the fluid control circuit between the inlet connection and the outlet connection preferably no fluidic connection is formed to a separate line that extends completely outside of the carrier parts, e.g. directly between two fluidic control components.

It is preferred, if each main fluid channel is formed by a first fluid channel cavity and the first carrier part and a second fluid channel cavity in the second carrier part respectively. Each first fluid channel cavity and/or second fluid channel cavity has preferably a semicircle-shaped cross-section. In doing so, in case of the established connection between the carrier parts, each main fluid channel can have a circular cross-section. At least some of the main fluid channels preferably have a substantially circular cross-section.

The fluid channel arrangement can comprise at least one fluidic branch channel branching of a main fluid channel. For example, in the first carrier part at least one fluidic branch channel can be present that extends between the first mounting surface and the first coupling surface. Accordingly, in the second carrier part at least one fluidic second branch channel can be present that extends between the second mounting surface and the second coupling surface.

For manufacturing of the carrier parts it is particularly advantageous, if the first carrier part and the second carrier part are formed by an injection mold part respectively. Preferably the injection mold parts are manufactured from a uniform material, particularly plastic or a compound material. In doing so, the first carrier part and the second carrier part are formed as integral carrier parts without seam and connection location. Particularly after manufacturing of the carrier parts, no material removing reworking is necessary for forming the fluid channels. Preferably all of the fluid channels of the fluid channel arrangement are formed during and by manufacturing of the carrier parts.

If at least one first branch channel is present in the first carrier part, the at least one first branch channel is at least in an extension direction from the first mounting surface to the first coupling surface or vice versa from the first coupling surface to the first mounting surface free of undercuts, the at least one first branch channel can be conical or cylindrical. If in the second carrier part at least one second branch channel is provided, the at least one second branch channel is at least in an extension direction from the second mounting surface to the second coupling surface or vice versa from the second coupling surface to the second mounting surface free of undercuts. The at least one second branch channel can be conical or cylindrical. In doing so, manufacturing of the carrier parts as injection mold parts is remarkably simplified.

Preferably all of the cutouts that extend transverse to the mounting surfaces and coupling surfaces, at least in a direction from the respective coupling surface to the respective mounting surface or vice versa from the respective mounting surface to the respective coupling surface are free of undercuts. The at least one first branch channel and/or the at least one second branch channel extend particularly in a die closure direction of an injection mold die for manufacturing the first carrier part or the second carrier part as injection mold part.

The manufacturing of the carrier parts as injection mold parts and/or the configuration of the at least one branch channel free of undercuts as explained above, is an independent aspect of the present invention and can particularly be provided independent from whether the fluid control components of the fluid control circuit and/or the components of the control circuitry are arranged at the mounting surfaces.

A seal arrangement for sealing the at least one main fluid channel is preferably arranged between the first coupling surface and the second coupling surface. The seal arrangement can comprise a ring seal for each present main fluid channel. If in the area of the separating location or the separating plane between the carrier parts multiple separate main fluid channels are formed, each of the main fluid channels is preferably completely surrounded by a ring seal of the seal arrangement in order to seal the main fluid channel with regard to the environment. For this a ring groove for inserting the ring seal can be present in the first coupling surface and/or in the second coupling surface. The ring groove can surround a first fluid channel cavity in the first coupling surface completely or the ring groove can surround a second fluid channel cavity in the second coupling surface completely.

It is further advantageous, if the first carrier part and/or the second carrier part is at least partly made of a transparent material in order to be able to judge by a visual check from outside in case of an established connection between the carrier parts whether the seal arrangement is correctly placed in the area of the separating location between the two carrier parts. Particularly it can be judged whether the at least one ring seal is correctly arranged in the respective ring groove.

Preferably all of the fluid control components of the fluid control circuit are arranged and particularly directly arranged at the first mounting surface. Additionally or alternatively, all of the electric and/or electronic components of the control circuitry are indirectly or directly arranged at the second mounting surface, preferably indirectly by means of a circuit board arrangement. Preferably no fluid flows through any of the components of the control circuitry.

It is advantageous, if a main fluid channel of the fluid channel arrangement forms a flow measurement channel. The flow measurement channel is particularly part of a flow measurement device of the fluid control arrangement. Preferably the flow measurement channel has a substantially circular cross-section along its complete extension. At least one pressure measurement channel pair with two pressure measurement channels is provided, the pressure measurement channels of which connect with the flow measurement channel at locations distant to each other in flow direction. The pressure measurement channels of a pressure measurement channel pair are preferably present in the same carrier part, can alternatively also be provided in different carrier parts. Preferably the pressure measurement channels extend at least in sections inside and through the second carrier part. In a preferred embodiment a separate pressure sensor is assigned to each of the pressure measurement channels. The pressure sensor is configured to measure the pressure inside the pressure measurement channel and thus at the connection location between the respective pressure measurement channel and the flow measurement channel. In an alternative configuration a difference pressure sensor is connected to the pressure measurement channels of a pressure measurement channel pair such that for each pressure measurement channel pair a single difference pressure sensor is sufficient. The difference pressure sensor is configured to create a difference pressure signal and to transmit it to the control unit.

At least one section of each pressure measurement channel can be formed by a branch channel, as described above. In a preferred embodiment a further section of each pressure measurement channel can extend in a nozzle that extends beyond the mounting surface and that is particularly integrally formed with the respective carrier part.

It is also advantageous, if a first pressure measurement channel pair as well as a second pressure measurement channel pair are provided, the pressure channels thereof connect with the same flow measurement channel. The flow measurement channel has preferably a first channel section with a first flow cross-section and a second channel section with a second flow cross-section, wherein the two flow cross-sections are different from each other and particularly have different amounts. The pressure measurement channels of the first pressure measurement channel pair connect with the first channel section and the pressure measurement channels of the second pressure measurement channel pair connect with the second channel section. In this configuration the possibility is provided to realize a flow measurement with each pressure measurement channel pair, wherein different measurement ranges for determination of the volume flow or the mass flow of the fluid flow are possible, due to the different flow cross-sections. Thus, the provided total measurement range is increased.

For determination of the volume flow of the mass flow of the fluid through the flow measurement channel, preferably an evaluation unit of the control circuitry is provided to which the measured pressure values of at least one pressure measurement channel pair can be transmitted. Due to the tube friction in the flow measurement channel, a difference pressure is created between the pressure measurement channels of a common pressure measurement channel pair, wherein the difference pressure is characteristic for the volume flow or the mass flow of the fluid through the flow measurement channel, which can be determined in the evaluation unit in doing so.

The above-explained configuration of the flow measurement device particularly the flow measurement channels and/or the pressure measurement channels and/or the connected pressure sensor can be realized in addition or as an alternative to the other aspects of the invention.

It is also preferred that the fluid control circuit comprises a series connection of an actuator, particularly a proportional valve, as well as a flow measurement device. The flow measurement device can be configured preferably as described above. In flow direction the flow measurement device is preferably arranged before the actuator. In doing so, a measurement independent from the load, e.g. a surgical instrument, connected to the outlet connection is guaranteed.

It is further advantageous, if the flow measurement device is arranged in flow direction between a pressure limiting device or a pressure control device or a pressure regulation device and the actuator. Preferably between the pressure limiting device or the pressure control device or the pressure regulation device and the actuator, no additional fluid control components are present, particularly no fluid control components that modify the fluid pressure—that are not part of the flow measurement device.

The circuit configuration of the fluid control circuit with regard of the hydraulic connection diagram, particularly the arrangement of the flow measurement device in series to the further fluid control components, can be used independent or in addition to the above-mentioned features of the fluid control arrangement and is particularly independent from whether the component of the fluid control circuit and/or the control circuitry are arranged at the mounting surfaces of the carrier parts.

BRIEF DESCRIPTION OF THE FIGURES

Preferred embodiments of the invention can be derived from the dependent claims and the drawings. In the following preferred embodiments of the invention are explained in detail with reference to the attached drawings. The drawing show:

DETAILED DESCRIPTION

Figure 1:
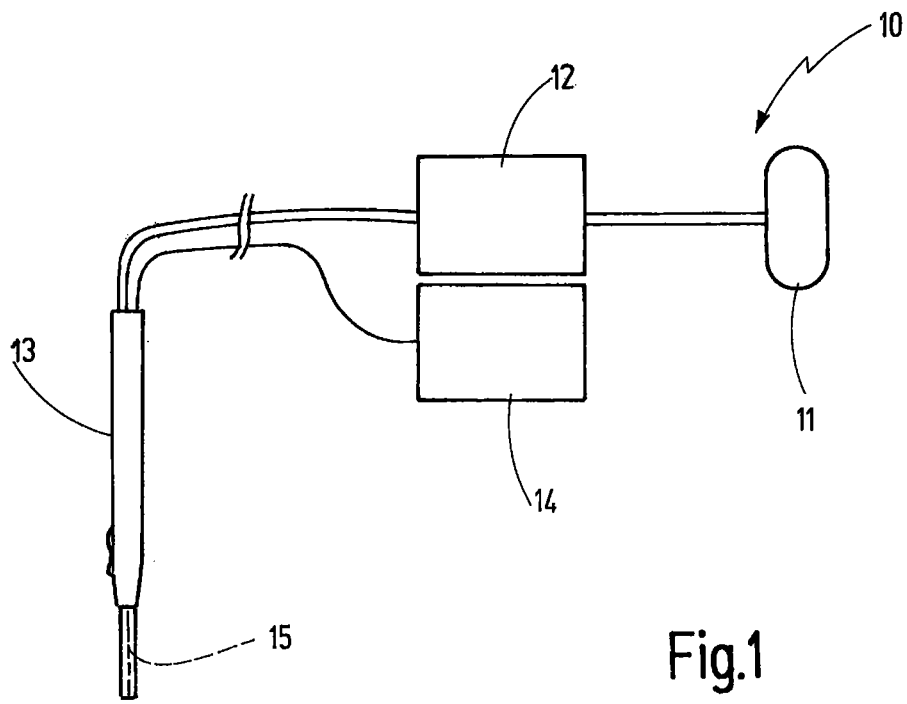
FIG. 1 a block diagram of an embodiment of a medical device in the form of an argon plasma coagulation device, FIG. 2 a hydraulic block diagram of an embodiment of a fluid control circuit for the device of FIG. 1, FIG. 3 a schematic basic illustration of an embodiment of a fluid control arrangement comprising a fluid control circuit and a control circuitry that are arranged at carrier parts, FIG. 4 a schematic illustration of an embodiment of a first carrier part in a top view on a first coupling surface of the first carrier part, as well as a schematic illustration of an embodiment of a seal arrangement, FIG. 5 the first carrier part of FIG. 4 in a cut section according to the cutting line V-V in FIG. 4, FIG. 6 a schematic illustration of an embodiment of the second carrier part in a top view on the second coupling surface of the second carrier part, FIG. 7 the second carrier part according to FIG. 6 in a schematic side view according to arrow VII in FIG. 6, FIG. 8 a schematic cut illustration through the carrier parts of the fluid control arrangement according to FIG. 3 that are connected with each other, FIG. 9 a basic illustration of the arrangement of a pressure sensor of the control circuitry and FIG. 10 a basic illustration of an embodiment of a flow measurement device of the fluid control arrangement.

FIG. 1 shows a medical device 10 that is configured as an argon plasma coagulation device as an example. The medical device 10 comprises a fluid source 11, to which a fluid control arrangement 12 is fluidically connected. An instrument can be connected to the fluid control arrangement 12 through which a fluid flow can be channeled that is provided by the fluid control arrangement 12. In the illustrated embodiment of the medical device 10, in addition a high voltage source 14 is present for providing high voltage for the instrument 13. The instrument 13 can be electrically connected with the high voltage source 14.

In the embodiment an argon gas flow for the instrument 13 is provided by the fluid control arrangement 12 that flows around an electrode 15 at the outlet end of the instrument 13. High voltage can be applied to the electrode 15 for argon plasma coagulation.

The medical device shown in FIG. 1 is only an example. The inventive fluid control arrangement 12 can also be used for other medical devices 10.

The fluid control arrangement 12 comprises a fluid control circuit 19 and a control circuitry 20. The fluid control circuit 19 comprises at least one and in the embodiment multiple fluid control components 21 that are fluidically connected to a fluid channel arrangement 22 of the fluid control circuit 19. The fluid channel arrangement 22 and the fluid control components 21 provide a fluidic connection between an inlet connection 23 and an outlet connection 24 of the fluid control arrangement 12 or the fluid control circuit 19 respectively. A fluid source 11 can be fluidically connected to the inlet connection 23. The instrument 13 can be fluidically connected to the outlet connection 24.

A fluid flows through the fluid control components 21. In the embodiment the fluid control circuit 19 comprises a switching valve 26, a pressure regulation valve 27 and a proportional valve 28 as actuators. As an option the fluid control circuit 19 can also comprise a filter 29. The filter 29 is preferably arranged downstream directly adjacent to the inlet connection 23.

Figure 2:
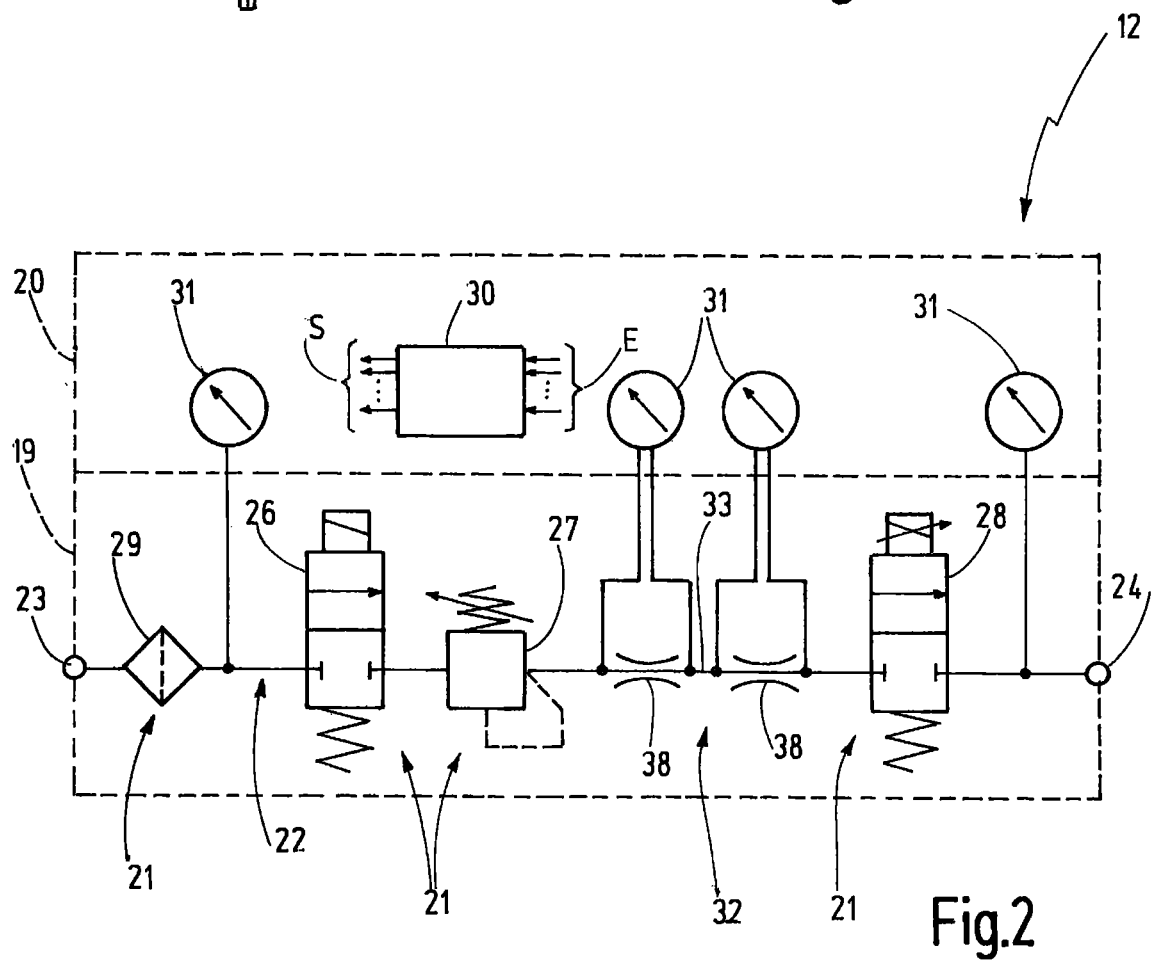

In the embodiment the control circuitry 20 comprises a control 30 that provides at least one control signal S for the at least one controllable fluid control component 21. According to the example, at least the switching valve 26 and the proportional valve 28 can be controlled by a control signal S of the control unit 30 respectively. At least one input signal E can be transmitted to the control unit 30. The at least one input signal E can be, e.g. a sensor signal or a measurement signal. In the embodiment illustrated in FIG. 2 multiple sensor units 31 are present that provide different input signals E in the form of sensor signals. For example, the inlet pressure adjacent to the inlet connection 23 or the filter 29 and the outlet pressure at the outlet connection 24 can be detected by respective pressure sensors and transmitted to the control unit 30.

In addition, in the embodiment the fluid control arrangement 12 comprises a flow detection device 32 that detects a volume flow or mass flow along a flow measurement channel 33 of the fluid channel arrangement 22 or signals characterizing the volume flow or the mass flow. According to the hydraulic scheme of FIG. 2, the fluid control circuit 19 comprises a circuit arrangement, in which the flow detection device 32 is arranged upstream of the proportional valve 28. The proportional valve 28 that forms the actuator for control of the mass or the volume flow to the instrument 13 is preferably arranged upstream directly before the outlet connection 24. According to the example, the pressure regulation valve 27 is arranged upstream of the flow detection device 32 such that upstream of the flow detection device 32, a predefined fluid pressure is present that is applied at the inlet of the flow measurement channel 33. Upstream of the pressure regulation valve 27 the switching valve 26 is arranged by means of which the fluid flow can be unblocked or blocked.

In the embodiment the flow detection device 32 comprises two sensor units 31 that detect a difference pressure between two distant measurement locations in the flow measurement channel 33 and transmit the different pressure to the control unit 30. Based on the different pressure, the control unit 30 can determine a volume flow measurement value or a mass flow measurement value of the fluid flowing through the flow measurement channel 33. According to the example the measurement locations of the two sensor units 31 are in different channel sections with different flow cross-sections. In doing so, the total measurement range for determination of the mass or volume flow can be increased.

Figure 10:
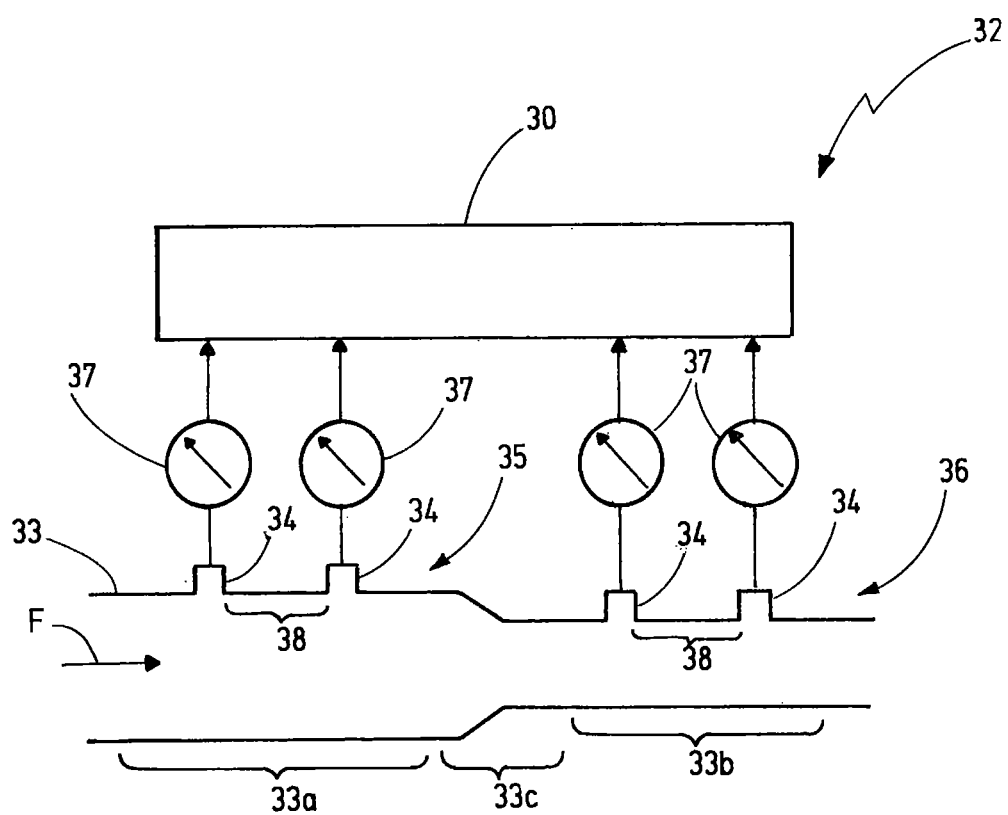

An embodiment for the flow detection device 32 is schematically illustrated in FIG. 10. The flow measurement channel 33 comprises a first channel section 33a, a second channel section 33b and a connection channel section 33c arranged in between. In the flow direction F of the fluid the first channel section 33a, the connection channel section 33c and the second channel section 33b are arranged in series. The first channel section 33a has a larger flow cross-section than the second channel section 33b. In the area of the connection channel section 33c the flow cross-section of the flow measurement channel 33 reduces. The cross-sectional contour of the flow measurement channel 33 is preferably substantially circular.

In the first channel section 33a two pressure measurement channels 34 of a first pressure measurement channel pair 35 open out with distance to each other in flow direction F. In the second channel section 33b of the flow measurement channel 33 two pressure measurement channels 34 of second pressure measurement channel pair 36 open out with distance in flow direction F. Within each of the channel sections 33a, 33b the flow cross-section of the flow measurement channel 33 does not change. Due to the friction of the fluid during flow along the flow measurement channel 33, a pressure loss between the pressure measurement channels 34 of the respective pressure measurement channel pair 35, 36 is created. A pressure sensor 37 is connected to each pressure measurement channel 34, wherein each pressure sensor 37 creates a pressure signal that corresponds to the pressure of the fluid at the location at which the respective pressure measurement channel 34 connects with the flow measurement channel 33, and wherein each pressure sensor 37 supplies the pressure signal to the control unit 30. The respective measurement aperture 38 is formed in this embodiment by the channel wall of the respective channel section 33a between the connection locations of the pressure channels 34 of a common pressure measurement channel pair 35 or 36. In the control unit 30 a mass flow value or a volume flow value for the fluid flowing through the flow measurement channel 33 can be determined from two pressure signals, particularly from two pressure signals of the pressure sensors 37 that are part of a common pressure measurement channel pair 35 or 36.

It is also possible to connect a difference pressure sensor to the pressure measurement channels 34 of one or all of the pressure measurement channel pairs 35 or 36.

The above-described hydraulic arrangement of the fluid control components 21 in the fluid control circuit 19 with regard to the flow direction F forms an aspect of the invention that can be realized independent from the further aspects described in the following. Through the arrangement of the flow detection device 32 upstream from the proportional valve 28 forming the actuator, the measurement of the volume flow or the mass flow can be carried out independent from the load that is according to the example formed by the instrument 13. The adjustment of the proportional valve 28 is known in the control unit 30, because the adjustment is defined by a control signal S of the control unit 30. The adjustment can be considered during determination of the volume or mass flow value as necessary.

Further, additional or alternative aspects of the inventive fluid control arrangement 12 refer to the compact and simple configuration and/or the manufacturing and/or the assembly of the fluid control arrangement 12. These inventive aspects are explained in the following with reference to FIGS. 3-9.

FIG. 3 schematically illustrates an embodiment for the mechanical configuration of the fluid control arrangement 12. In this embodiment the fluid control arrangement 12 comprises a first carrier part 45 with a first mounting surface 46 and a first coupling surface 47, as well as a second carrier part 48 with a second mounting surface 49 and a second coupling surface 50. In this embodiment the first mounting surface 46 is configured to support the at least one fluid control components 21 of the fluid control circuit 19. The fluid control components 21 can be particularly directly attached to the first mounting surface, as illustrated in FIG. 3. The first mounting surface and the first coupling surface 47 are, according to the example, opposite sides of the first carrier part 45. Accordingly, the second mounting surface 49 and the second coupling surface 50 are opposite sides of the second carrier part 48.

Preferably the first mounting surface 46 and/or the second mounting surface 49 extends within a plane. The first coupling surface 47 has, according to the example, a particularly continuous planar surface section 47a that extends in a plane that is preferably orientated parallel to the plane, in which the first mounting surface 46 extends. The second coupling surface 50 has, according to the example, a particularly continuous planar surface section 50a that extends in a plane that is preferably orientated parallel to the plane, in which the second mounting surface 49 extends. The carrier parts 45, 48 can be shaped as plates or cuboids for example.

The coupling surfaces 47, 50 are configured to establish a connection between the two carrier parts 45, 48, wherein the planar surface sections 47a, 50a of the coupling surfaces 47, 50 can abut each other or can be arranged facing each other under formation of a gap.

The second mounting surface 49 is for example configured to support at least one electric and/or electronic component of the control circuitry 20. As illustrated in FIG. 3, multiple and preferably all of the electric and/or electronic components 51 of the control circuitry 20 are arranged on a circuit board arrangement 52 that is attached to the second mounting surface 49. The circuit board arrangement 52 comprises multiple component supporting circuit board sections 53 that are electrically and mechanically connected with each other via flexible connecting sections 54. The flexible connecting sections 54 are integral part of the two component supporting circuit board sections 53 that are connected with each other by the respective flexible connecting section 54. The circuit board arrangement 52 is thus integrally formed as a whole and plugs and plug connections with connection cables between the circuit board sections 53 can be avoided.

It is additionally preferred, if the electric and/or electronic components 51 of the control circuitry 20 are arranged at the side of the circuit board arrangement 52 that faces the second mounting surface 49. Preferably at the lower side of the circuit board arrangement 52 facing away from the second mounting surface 49, no electric and/or electronic components 51 are present. In doing so, the components 51 are arranged in a protected manner in the interstice between the circuit board arrangement 52 and the second carrier part 48, which simplifies handling during the assembly.

As it can also be seen in FIG. 3, one or more electric control lines 55 can lead from the control circuitry 20 to one or more of the fluid control components 21, according to the example, to the switching valve 26 and the proportional valve 28. Via these control lines 55 a control of the respective fluid control components 21 by means of the control circuitry 20 is facilitated.

In the embodiment the control unit 30, as well as pressure sensors 37 of the flow detection device 32 and as an option, additionally the pressure sensors for detecting the inlet pressure and/or the outlet pressure (compare FIG. 2) are part of the at least one electric and/or electronic component 51 of the control circuitry 20.

The circuit board arrangement 52 and according to the example the component supporting circuit board sections 53 are connected with the mounting surface 49 via one or more mounting pins 56 according to the example. According to the example, the mounting pins 56 are integral part of the second carrier part 48 and extend substantially orthogonal away from the second mounting surface 49. Preferably each mounting pin 56 can have a circular cross-section and can have an inner thread at its free end. In the component supporting circuit board sections mounting holes can be present that correspond to the arrangement pattern of the mounting pins 56. The component supporting circuit board sections 53 can be brought into contact with the free ends of the mounting pins 56 and can be attached by means of screws or other suitable attachment means, as schematically illustrated in FIG. 3.

The first coupling surface 47 of the first carrier part 45 has at least one first fluid channel cavity 60 and in the embodiment multiple first fluid channel cavities 60. The first fluid channel cavities 60 are formed by groove-like depressions that are deepened relative to the planar surface section 47a of the first coupling surface 47. In the cross-section orthogonal to their extension direction, the first fluid channel cavities 60 are preferably semicircle-shaped. In the embodiment each fluid channel cavity 60 extends linearly. Alternative to the preferred embodiment, one or more of the first fluid channel cavities 60 can also have an arc-shaped or curved extension in its extension direction along the first coupling surface 47.

In the first carrier part 45 additionally multiple first branch channels 61 are present that extend from the first coupling surface 47 to the first mounting surface 46. In the embodiment the first branch channels 61 respectively open into one of the first fluid channel cavities 60. Preferably at least two first branch channels 61 open in each first fluid channel cavity 60. By the first branch channels 61 a fluid connection between one or more of the fluid control components 21 and the first fluid channel cavities 60 can be established.

In the second coupling surface 50 of the second carrier part 48 multiple second fluid channel cavities 62 are present according to the example. The second fluid channel cavities 62 can be configured according to the first fluid channel cavities 60 and for groove-like depressions according to the example with a preferably semicircle-shaped cross-section orthogonal to their extension. The second fluid channel cavities 62 are deepened with reference to the planar surface section 50a of the second coupling surface 50.

In the second carrier part 48 second branch channels 63 can be present that extend completely between the second mounting surface 49 and the second coupling surface 50 and open into one or more of the second fluid channel cavities 62. In the illustrated embodiment all of the second branch channels 63 open into one single second fluid channel cavity 62, wherein these two second branch channels 63 form a pressure measurement channel 34 of the flow detection device 32 respectively or are part of the respective pressure measurement channel 34. In the illustrated embodiment each pressure measurement channel 34 comprises a section that opens into the second fluid channel cavity 62 that is formed by the second branch channel 63, wherein a further section of the pressure measurement channel 34 adjoins the second branch channel 63 that is formed within a nozzle 64. The nozzle 64 extends obliquely or orthogonal away from the second mounting surface 49 to a free end 65. At this free end 65 a pressure sensor 37 assigned to the pressure measurement channel 34 is fluidically coupled with the pressure measurement channel 34.

Figure 9:
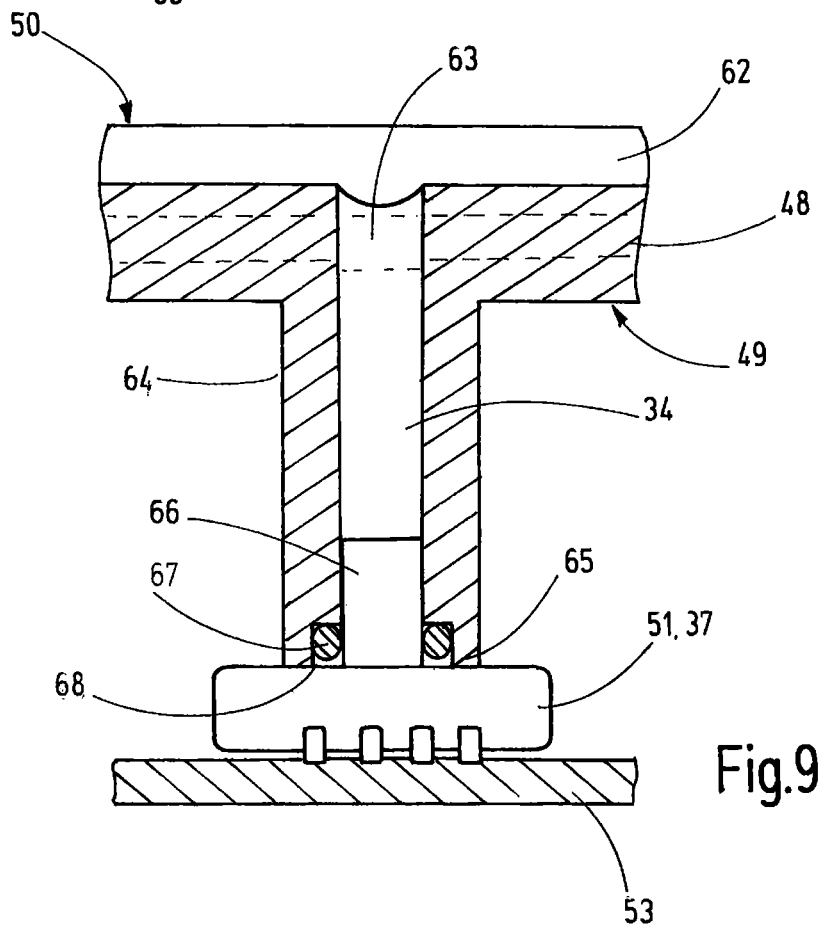

The arrangement of the pressure sensor in the nozzle 64 is schematically illustrated in FIG. 9. According to the example, the pressure sensor 37 comprises a measuring element 66 that extends into the pressure measurement channel 34 and is surrounded by a radial seal element 67 in a ring-shaped manner. The radial seal element 67 is seated in a ring cavity 68 in the region of the free end 65 of the nozzle 64. It is supported at the circumferential wall of the ring cavity 68 at the radial outer side and at the measuring element 66 at the radial inner side, in order to create a radial seal effect in this manner. As it can be seen in FIG. 7, all of the pressure sensors 37 of the flow detection device 32 are arranged at a separate nozzle 64 respectively and are preferably supported by a common component-supporting circuit board section 53.

Figure 8:
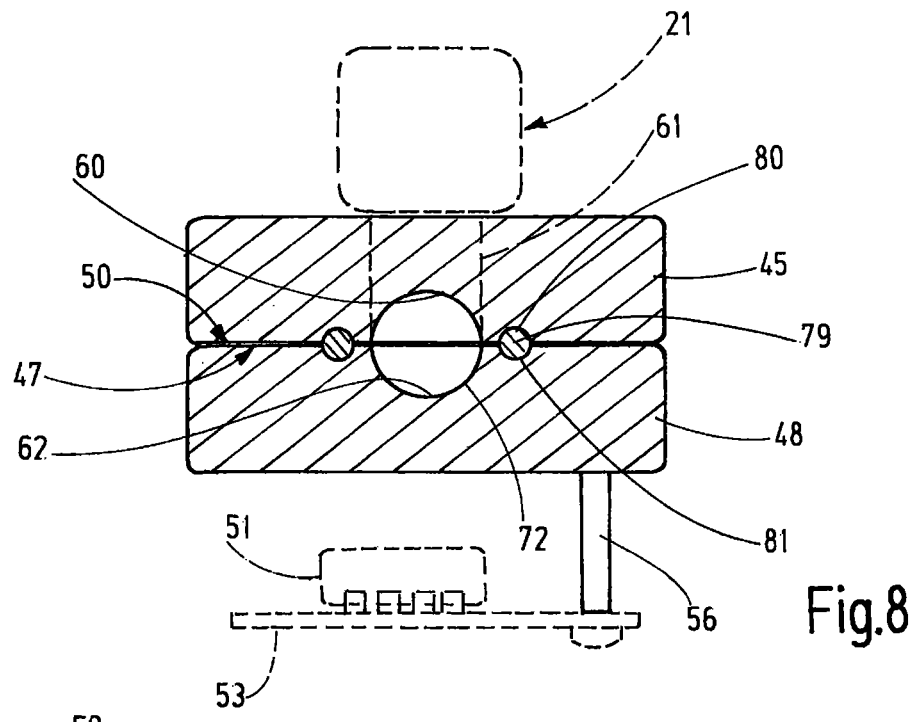

The two carrier parts 45, 48 are mechanically connected with each other with facing coupling surfaces 47, 50, wherein the planar surface section 47a of the first coupling surface 47 can abut at the planar surface section 50a of the second coupling surface 50 or can be arranged under formation of a gap or an interstice. According to the example, the first fluid channel cavity 60 and the second fluid channel cavity 62 are selected such that each of the first fluid channel cavity 60 forms or limits with one second fluid channel cavity 62 in the area of the separation plane or separation location between the two carrier parts 45, 48 one main fluid channel 72 (FIG. 8). Because, according to the example, four first fluid channel cavities 60 and four second fluid channel cavities 62 are provided, four main fluid channels 72 are obtained.

One of these main fluid channels 72 forms a flow measurement channel 33. As it can be seen in FIGS. 4 and 6, one of the first fluid channel cavities 60 and the assigned second fluid channel cavity 62, each comprise a section with a larger cross-section and each comprise a section with a smaller cross-section that are connected with each other by a tapering section. The fluid channel cavities can be named as first measurement channel cavity 73 or as second measurement channel cavity 74. The two pressure measurement channels 34 of the first pressure measurement channel pair 35 and the two pressure measurement channels 34 of the second pressure measurement channel pair 36 open into the second measurement channel cavity 74. For the further configuration of the flow detection device 32 reference is made to the explanations above, particularly under reference to FIGS. 2 and 10.

In modification to the illustrated preferred embodiment, it is also possible that a first fluid channel cavity 60 limits with the planar surface section 50a of the second coupling surface 50, a main fluid channel 72 and/or that a second fluid channel cavity 62 limits a main fluid channel 72 with the planar surface section 47a of the first coupling surface 47. Thus, it is not necessary that coinciding first and second fluid channel cavities 60 and 62 are present for forming the main fluid channel 72.

For sealing the two carrier parts 45, 48 in the area of the coupling surfaces 47, 50, a seal arrangement 78 is present that is illustrated in FIG. 4 as an example. In the embodiment the seal arrangement 78 has multiple separate ring seals 79. In the embodiment each ring seal 79 is inserted in a first ring groove 80 at the first coupling surface 47 of the first carrier part 45. The first ring groove 80 surrounds one respective first fluid channel cavity 60 completely. The first ring groove 80 is dimensioned such that the inserted ring seal 79 extends out of the ring groove 80 and projects beyond the planar surface section 47a of the first coupling surface 47.

In the embodiment also in the second coupling surface 50, second ring grooves 81 are present that completely surround one respective second fluid channel cavity 62. The second ring grooves 81 can be configured according to the first ring grooves 80. If the first carrier part 45 and the second carrier part 48 are connected with each other by means of their facing coupling surfaces 47, 50, each ring seal 79 is seated in a first ring groove 80 and in a second ring groove 81, as schematically illustrated in FIG. 8. In doing so, a very good positioning of the ring seal 79 and a respective sealing effect can be guaranteed.

In modification to the preferred embodiment, also only at least one ring groove 80 or 81 could be present in one of the carrier parts 45, 48 in order to seal a main fluid channel 72 after assembly of the carrier parts 45, 48. In a further modification a plate-like seal element could be arranged between the two carrier parts 45, 48 that comprises respective through openings in the area of the first fluid channel cavities 60 and the second fluid channel cavities 62 and abuts around the first fluid channel cavities 60 and the second fluid channel cavities 62 at the planar surface sections 47a, 50a of the coupling surfaces 47, 50.

In another embodiment the seal arrangement 78 could also be connected with one of the carrier parts 45, 48 by means of a substance bond or adhesive bond. For example, the seal arrangement 78 could be glued to one of the coupling surfaces 47, 50 or could be attached to one of the carrier parts 45, 48 during manufacturing of the carrier part 45, 48 by means of a two-component injection molding.

In a preferred embodiment the carrier parts 45, 48 are at least in the region of their coupling surfaces 47, 50 or alternatively completely made of a transparent material. In doing so, a visual check can be executed in the attached assembled condition whether the ring seals 79 are correctly arranged in the respectively assigned ring grooves 80 or 81 and whether the seal effect can be guaranteed.

A further independent aspect of the inventive fluid control arrangement 12 refers to the manufacturing of the carrier parts 45, 48. Preferably the carrier parts 45, 48 are configured as injection mold parts. In doing so, the mold closure direction is preferably selected such that the mold closure direction coincides with the extension direction of the branch channels 61, 63. In injection molding the mold closure direction is the direction in which the two mold parts are moved relative to each other for closing of the injection mold or for opening the injection mold.

Each branch channel 61, 63 of a carrier part 45, 48 is configured free of undercuts in an extension direction from one end to the respective other end. In this extension direction each branch channel 61, 63 can be configured in a conically tapering manner. Each first branch circuit 61 extends free of undercuts either originating from the first mounting surface 46 to the first coupling surface 47 or vice versa from the first coupling surface 47 to the first mounting surface 46. Corresponding to this, each second branch channel 63 extends free of undercuts from the first coupling surface 50 to the first mounting surface 49 or to the free end of the nozzle 64 or vice versa from the free end of the nozzle 64 or from the second mounting surface 49 to the second coupling surface 50. Due to this, configuration of the branch channels 61, 63 being free of undercuts, the carrier part 45, 48 can be configured as injection mold part in a very simple manner.

The invention refers to a fluid control arrangement 12 for a medical device 10, particularly a medical device for argon plasma coagulation. The fluid control arrangement 12 has a fluid control circuit 19 with at least one fluid control component 21, through which a fluid flows. For control of the at least one fluid control component 21, a control circuitry 20 with at least one electric and/or electronic component 51 is provided. A first carrier part 45 has a first coupling surface 47 and a second carrier part 48 has a second coupling surface 50. In the first coupling surface 47 at least one first fluid channel cavity 60 and/or in the second coupling surface 50 at least one second fluid channel cavity 62 is provided. During connection of the carrier parts 45, 48 with coupling surfaces 47, 50 facing each other, in the area of the separation location at least one main fluid channel 72 is formed. Each main fluid channel 74 is thus partly limited by the first carrier part 45 and partly by the second carrier part 48. At the first carrier part 45 a first mounting surface 46 for the at least one fluid control component 21 can be present. At the second carrier part 48 a second mounting surface 49 for the at least one electric and/or electronic component 51 of the control circuitry 20 can be present. In addition or alternative to the mounting of the components at the mounting surfaces 46, 49, the carrier parts 45, 48 can be configured as injection mold parts. Another independent aspect refers to the hydraulic connection in the fluid control circuit 19, wherein a flow detection device 32 upstream of an actuator is arranged via which the fluid flow out of an outlet connection 24 of the fluid control arrangement 12 can be controlled or feedback controlled by control of the control circuitry 20.

The invention claimed is:

1. A fluid control arrangement for a medical device, the fluid control arrangement comprising:
a fluid control circuit comprising at least one fluid channel arrangement and at least one fluid control component that are arranged between an inlet connection and an outlet connection;
a controller configured to control the at least one fluid control component;
a first carrier part comprising a first coupling surface having a first fluid channel cavity;
a second carrier part comprising a second coupling surface having a second fluid channel cavity;
wherein first and second coupling surfaces and the first and second fluid channel cavities extend along a common plane; and
wherein the first fluid channel cavity and the second fluid channel cavity form a main fluid channel of the fluid channel arrangement when aligned with one another.

2. The fluid control arrangement of claim 1, wherein the first and second fluid channel cavities have a substantially semicircle cross-section.

3. The fluid control arrangement of claim 1, wherein the first carrier part and the second carrier part are formed by a respective injection mold part.

4. The fluid control arrangement of claim 1, further comprising at least one fluidic first branch channel that extends away from the first coupling surface and is fluidly connected to the main fluid channel.

5. The fluid control arrangement of claim 1, further comprising at least one fluidic second branch channel that extends away from the second coupling surface and is fluidly connected to the main fluid channel.

6. The fluid control arrangement of claim 1, further comprising a seal arrangement arranged between the first coupling surface and the second coupling surface.

7. The fluid control arrangement of claim 1, wherein the first and second coupling surfaces each have at least one additional fluid channel cavity that form at least an additional fluid channel when aligned.

8. The fluid control arrangement of claim 7, further comprising a seal arrangement comprising at least one ring surrounding one of the main fluid channel or additional fluid channel.

9. The fluid control arrangement of claim 1, wherein the fluid control component is coupled to the first carrier part by a first mounting surface opposite the first coupling surface.

10. The fluid control arrangement of claim 1, further comprising an electrical component coupled to the second carrier part by a second mounting surface.

11. The fluid control arrangement of claim 1, further comprising a first pressure measurement channel fluidly connected to the main fluid channel.

12. The fluid control arrangement of claim 11, further comprising a first pressure sensor coupled to the at least one pressure measurement channel.

13. The fluid control arrangement of claim 11, further comprising a second pressure measurement channel having a cross-section different than a cross-section of the first pressure measurement channel.

14. The fluid control arrangement of claim 13, further comprising a second pressure sensor fluidly connected to the second pressure measurement channel, wherein the first and second pressure sensors are electrically coupled to a control unit.

* * * * *